United States Patent
English et al.

(10) Patent No.: US 11,682,872 B2
(45) Date of Patent: Jun. 20, 2023

(54) CONTACT FOR A MEDICAL CONNECTOR ASSEMBLY

(71) Applicant: Cardiac Pacemakers, Inc., St. Paul, MN (US)

(72) Inventors: James Michael English, Cahir (IE); Robert Allen Jones, Lake Elmo, MN (US); Scott A. Spadgenske, Buffalo, MN (US); Moira B. Sweeney, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 207 days.

(21) Appl. No.: 17/173,583

(22) Filed: Feb. 11, 2021

(65) Prior Publication Data

US 2021/0257792 A1 Aug. 19, 2021

Related U.S. Application Data

(60) Provisional application No. 62/976,731, filed on Feb. 14, 2020.

(51) Int. Cl.
*H01R 13/514* (2006.01)
*H01R 24/58* (2011.01)
(Continued)

(52) U.S. Cl.
CPC ............ *H01R 24/58* (2013.01); *H01R 13/33* (2013.01); *H01R 13/514* (2013.01);
(Continued)

(58) Field of Classification Search
CPC ...... H01R 24/58; H01R 13/33; H01R 13/514; H01R 13/5202; H01R 13/5224; H01R 2103/00; H01R 2201/12; Y10S 439/909
See application file for complete search history.

(56) References Cited

U.S. PATENT DOCUMENTS 2,450,529 A * 10/1948 Sprigg .................. H01R 13/111
29/446
2,900,631 A * 8/1959 Love ...................... H04N 5/645
248/316.1
(Continued)

FOREIGN PATENT DOCUMENTS

CN 115427107 A 12/2022
WO WO-2021163261 A1 8/2021

OTHER PUBLICATIONS

"International Application Serial No. PCT/US2021/017565, International Preliminary Report on Patentability dated Aug. 25, 2022", 8 pgs.
(Continued)

*Primary Examiner* — Tho D Ta
(74) *Attorney, Agent, or Firm* — Schwegman Lundberg & Woessner, P.A.

(57) ABSTRACT

A connector apparatus for a medical device includes a cylindrical core of nonconductive material, a beam of conductive material, and a sleeve of conductive material. The cylindrical core includes an outside surface, an inside surface, a hollow center having a cross sectional area, and a slot opening in the cylindrical core extending from the outside surface to the inside surface. The beam is placed in the slot opening in the cylindrical core, wherein the beam reduces the cross-sectional area of the hollow center of the cylindrical core. The sleeve of conductive material is placed over the outside surface of the cylindrical core.

19 Claims, 7 Drawing Sheets

(51) Int. Cl.
*H01R 13/33* (2006.01)
*H01R 13/52* (2006.01)
*A61N 1/375* (2006.01)
*H01R 103/00* (2006.01)

(52) U.S. Cl.
CPC ..... *H01R 13/5202* (2013.01); *H01R 13/5224* (2013.01); *A61B 2562/227* (2013.01); *A61N 1/3752* (2013.01); *H01R 2103/00* (2013.01); *H01R 2201/12* (2013.01)

(56) References Cited

U.S. PATENT DOCUMENTS

| | | | | |
|---|---|---|---|---|
| 4,695,116 A | * | 9/1987 | Bailey | H01R 24/58 |
| | | | | 439/668 |
| 5,203,813 A | * | 4/1993 | Fitzsimmons | H01R 43/16 |
| | | | | 439/843 |
| 5,667,409 A | * | 9/1997 | Wong | H01R 24/542 |
| | | | | 439/852 |
| 5,865,654 A | * | 2/1999 | Shimirak | H01R 24/44 |
| | | | | 439/654 |
| 6,464,546 B2 | * | 10/2002 | LaCoy | H01R 13/187 |
| | | | | 439/930 |
| 2005/0027325 A1 | | 2/2005 | Lahti et al. | |
| 2009/0233491 A1 | | 9/2009 | Barker et al. | |
| 2009/0264943 A1 | | 10/2009 | Barker | |
| 2012/0245664 A1 | | 9/2012 | Smith et al. | |
| 2015/0018909 A1 | | 1/2015 | Rebentisch et al. | |
| 2018/0369570 A1 | | 12/2018 | Oster et al. | |

OTHER PUBLICATIONS

"International Application Serial No. PCT/US2021/017565, International Search Report dated May 17, 2021", 4 pgs.
"International Application Serial No. PCT/US2021/017565, Written Opinion dated May 17, 2021", 6 pgs.

* cited by examiner

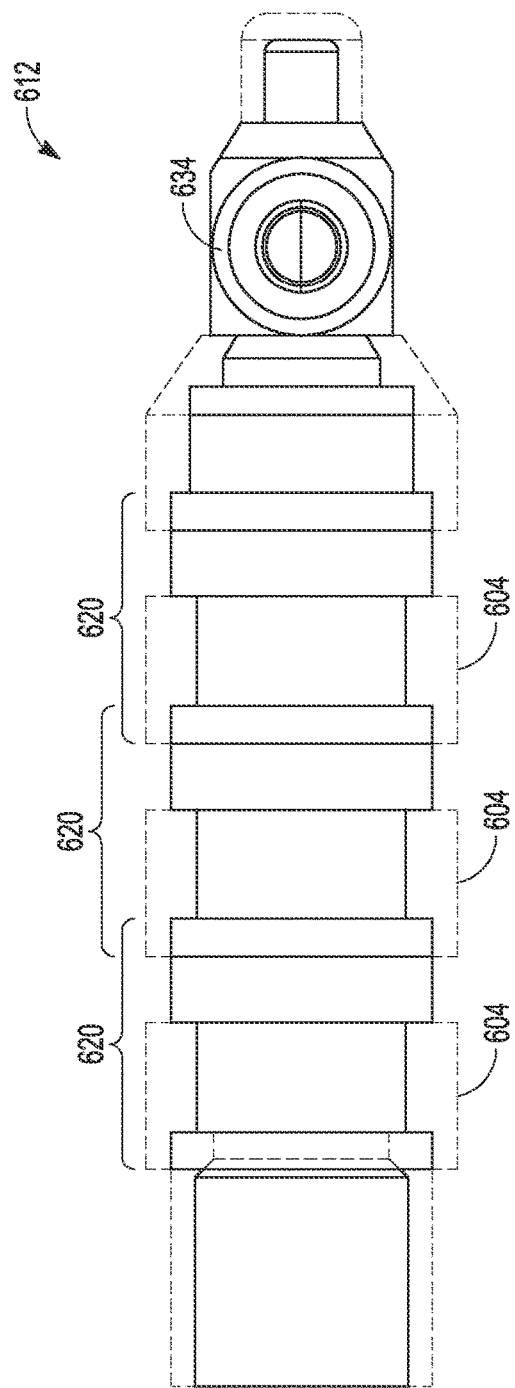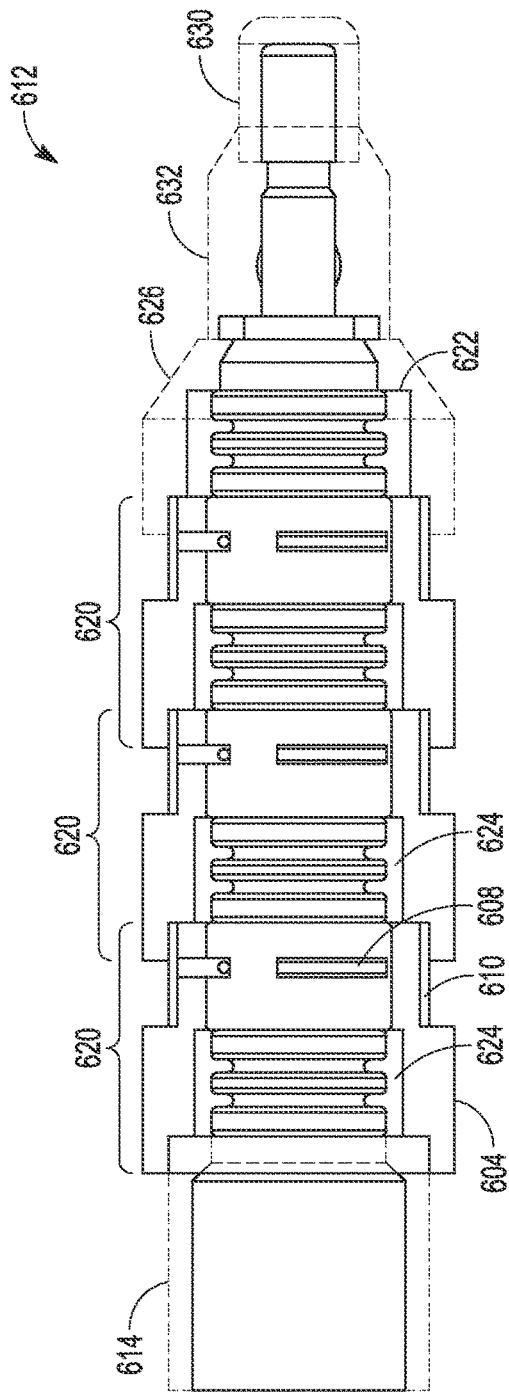

CONTACT FOR A MEDICAL CONNECTOR ASSEMBLY

CLAIM OF PRIORITY

This application claims the benefit of priority under 35 U.S.C. § 119(e) of U.S. Provisional Patent Application Ser. No. 62/976,731, filed on Feb. 14, 2020, which is herein incorporated by reference in its entirety.

TECHNICAL FIELD

This patent application relates to implantable medical devices and, in particular, a device connector for implantable leads.

BACKGROUND

Implantable medical devices or partially implantable medical devices can include a hermetically sealed metal case that houses electronic circuits. For some implantable or partially implantable cardiac rhythm management devices, electrically conductive implantable leads are used to sense electrical signals in the body of a patient, and to deliver electrical signals to the body as part of electrical therapy. Typically, the leads are implanted and then connected to the implantable or partially medical device. For ease of use for a physician, it is desired for the connector of the medical device to have a low insertion force, while for comfort and satisfaction of the patient it is desired for the connector to be robust and have a high resilience to fretting fatigue.

SUMMARY

This document relates to lead connector assemblies for medical devices. An example of a connector apparatus includes a cylindrical core, a beam of conductive material, and a sleeve of conductive material. The cylindrical core includes an outside surface, an inside surface, a hollow center having a cross sectional area, and a slot opening in the cylindrical core extending from the outside surface to the inside surface. The beam is placed in the slot opening in the cylindrical core, wherein the beam reduces the cross-sectional area of the hollow center of the cylindrical core. The sleeve of conductive material is placed over the outside surface of the cylindrical core.

An example of a connector assembly includes at least one modular core connector having a cylindrical shape and comprised of nonconductive material. The modular core connector includes an insertion portion having an outside diameter and including an outside surface, an inside surface, a hollow center having a cross sectional area, and a slot opening extending from the outside surface to the inside surface; a receiving portion having an inside diameter and an outside diameter greater than the outside diameter of the insertion portion; a beam of conductive material beam placed in the slot opening of the insertion portion, and at least a portion of the beam is arranged within the cross-sectional area of the hollow center of the insertion portion; and a sleeve of conductive material placed over the outside surface of the insertion portion An example of a header connector assembly includes multiple modular core connectors and a header block. Each modular core connector has a cylindrical shape and includes an insertion portion having an outside diameter and including an outside surface, an inside surface, a hollow center having a cross sectional area, and a slot opening extending from the outside surface to the inside surface; a receiving portion having an inside diameter and an outside diameter greater than the outside diameter of the insertion portion; a beam of conductive material beam placed in the slot opening of the insertion portion, and at least a portion of the beam is arranged within the cross-sectional area of the hollow center of the insertion portion; and a sleeve of conductive material placed over the outside surface of the insertion portion. The multiple modular core connectors are arranged within the header block and the header block includes multiple electrical contacts contacting the sleeve of conductive material of the multiple modular core connectors.

This summary is intended to provide an overview of the subject matter of the present application. It is not intended to provide an exclusive or exhaustive explanation of the invention. The detailed description is included to provide further information about the subject matter of the present patent application.

BRIEF DESCRIPTION OF THE DRAWINGS

FIGS. 6A-6C are illustrations of another example of a connector assembly for a medical device.

DETAILED DESCRIPTION

Figure 1:
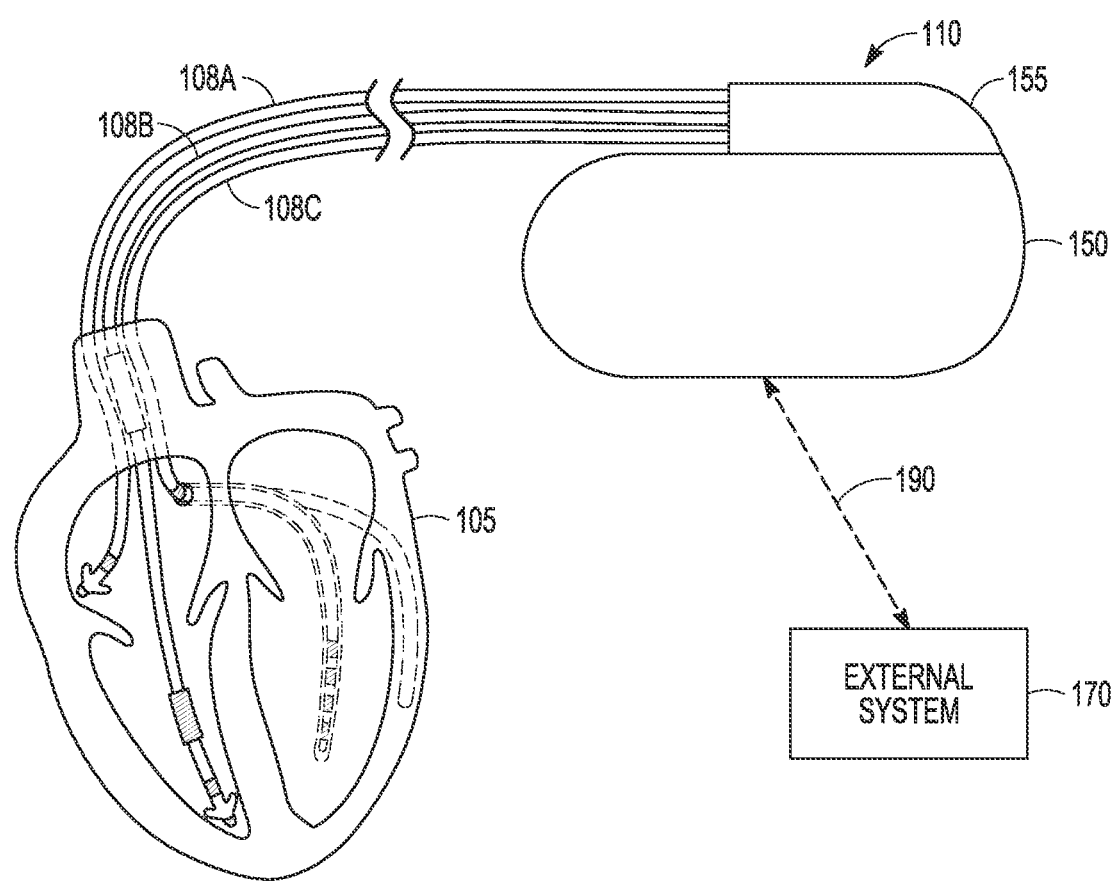
FIG. 1 is an illustration of portions of a system that uses an implantable medical device.

This document relates to a connector assembly for an ambulatory medical device. FIG. 1 is an illustration of portions of a system that uses an implantable medical device (IMD). Some examples of the IMD 110 include a pacemaker, a defibrillator, a cardiac resynchronization therapy (CRT) device, a combination of such devices, or a diagnostic-only device. The system also typically includes an IMD programmer or other external device 170 that communicates wireless signals 190 with the IMD 110, such as by using radio frequency (RF) or other telemetry signals.

The IMD 110 can be coupled by one or more conductive leads 108A-C to heart 105. The cardiac leads 108A-C in the example of FIG. 1 include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals. Sensed electrical cardiac signals can be sampled to create an electrogram. An electrogram can be analyzed by the IMD and/or can be stored in the IMD and later communicated to an external device where the sampled signals can be displayed for analysis.

The cardiac leads 108A-C include right atrial (RA) lead 108A, right ventricle (RV) lead 108B, and a third cardiac lead 108C for placement in a coronary vein lying epicardially on the left ventricle (LV) via the coronary vein.

The IMD 110 includes a hermetically-sealed IMD housing or can 150 that houses electronic circuits and a header connector 155. The cardiac leads 108A-C are connected to the IMD through the header connector 155. For implantable cardiac rhythm management devices, electrical signals sensed in the body and electrical signals delivered to the body need to pass through the hermetic seal. This is accomplished with feedthroughs. Feedthroughs are comprised of an electrical conductor, usually a pin, passing through insulating material and providing connection from circuitry internal to the can to a point external to the can while maintaining the hermetic seal. The header connector 155 provides the electrical connection between conductive leads and the feedthroughs. It is desired for a lead connector of a medical device (such as the header connector 155 in FIG. 1) to have a low insertion force and to provide a robust connection with high resilience to fretting fatigue.

Figure 2A:
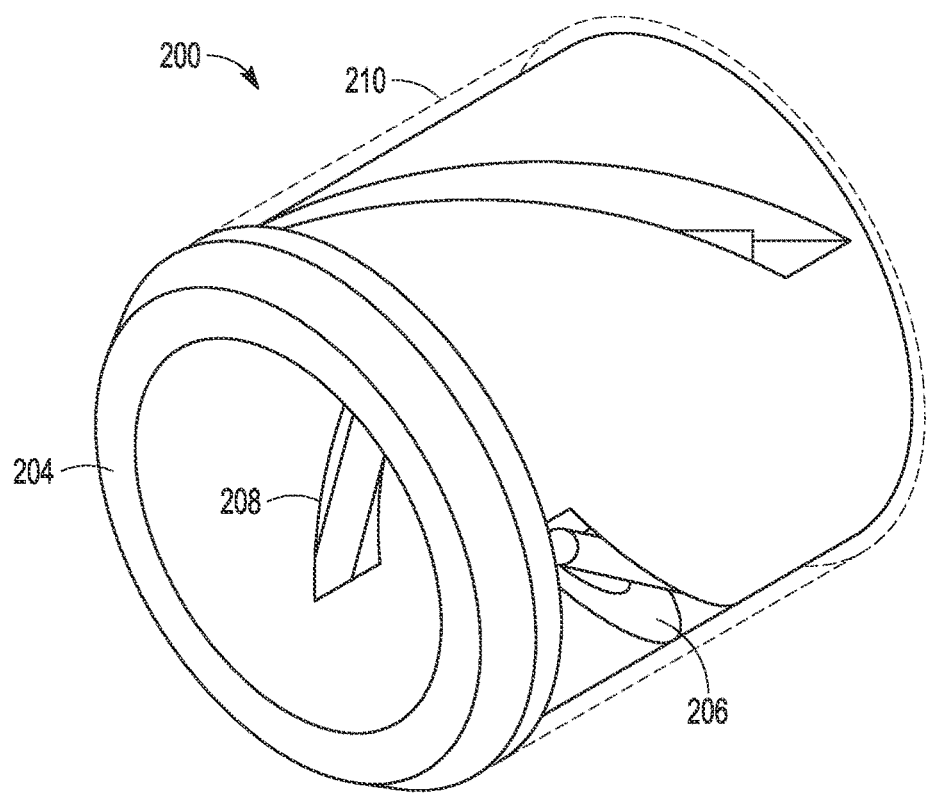
FIGS. 2A and 2B are two views of an example of a connector subassembly for a medical device.
Figure 2B:
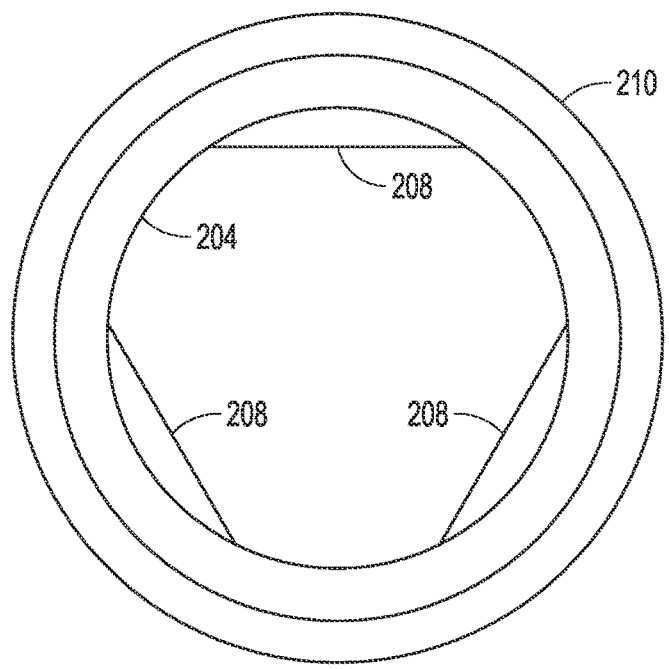

FIGS. 2A and 2B are two views of an example of a connector subassembly 202 of a connector for a medical device. The connector subassembly 202 provides a mechanical connection to a lead inserted into the connector subassembly 202 and provides electrical contact to the lead. The connector subassembly 202 includes a cylindrical core 204. The cylindrical core 204 can be comprised of conductive or nonconductive material. The cylindrical core 204 is barrel-shaped and has a hollow center or bore, and an inside surface and an outside surface. FIG. 2A shows that the cylindrical core 204 has one or more slots 206. The slots 206 extend from the outside surface to the inside surface of the core and the slots 206 have a length that runs in a direction diagonal to a center axis of the cylindrical core 204. In the example of FIG. 2A, the cylindrical core 204 has three slots.

The connector subassembly 202 also includes a beam 208 placed in the slots 206 of the cylindrical core. In the example of FIGS. 2A and 2B, there are three beam elements placed in the three slots. It can be seen in FIGS. 2A and 2B that when a beam 208 is placed in a slot 206, at least portion of the beam is arranged within the cross-sectional area of the hollow center. In FIG. 2B it can be seen that the three beams 208 reduce the cross-sectional area of the bore of the cylindrical core 204. The connector subassembly 202 also includes a sleeve 210 of conductive material placed over the outside surface of the cylindrical core 204. In some examples, the sleeve 210 is a hypo-tube. In other examples, the sleeve 210 is machined housing, stamped housing, or a metal injected molding (MIM) additive manufacturing. The conductive sleeve 210 is in electrical contact with the beams 208. The sleeve 210 may include slots that match the slots of the cylindrical core 204. When a beam is placed in the slots, the sleeve 210 may be twisted or rotated relative to the cylindrical core 204 to close the slots and hold the beam in place.

When the beam elements are placed in the slots, the beam elements are oriented somewhat transversely to the central axis of the cylindrical core. The ends of the beam elements are constrained by the sleeve 210. In certain examples, the beam elements are supported by the slots and housing, and in certain examples the ends of the beam elements are fixed, such as by welding for example.

A lead end is inserted into the connector subassembly 202 for connection. The lead may be used for one or more of pacing, sensing, and defibrillation by the medical device. The beam elements are flexible and form a three-point bending configuration to provide support for the lead end. In certain examples, the beam elements are formed by one wire fed into the slot openings. If there are three slot openings, the wire may include two or more bends to arrange the wire into the three slot openings. In certain examples, the beams free float between the sleeve 210 and inner retention walls of the inner slots of the cylindrical core 204. When a lead is inserted, the beam (e.g., a wire beam) is lifted up to contact the conductive sleeve 210.

The lead end elastically deforms the beam elements and the beam elements remain in their elastic deformation range. The lead end includes an electrical contact area and a beam element is conductive and provides a "crossed wire" point of contact with the electrical contact area of the lead end. The stresses on a beam element cause it to remain in its elastic deformation range so that the contact load is consistent through multiple lead insertions.

Figure 3:
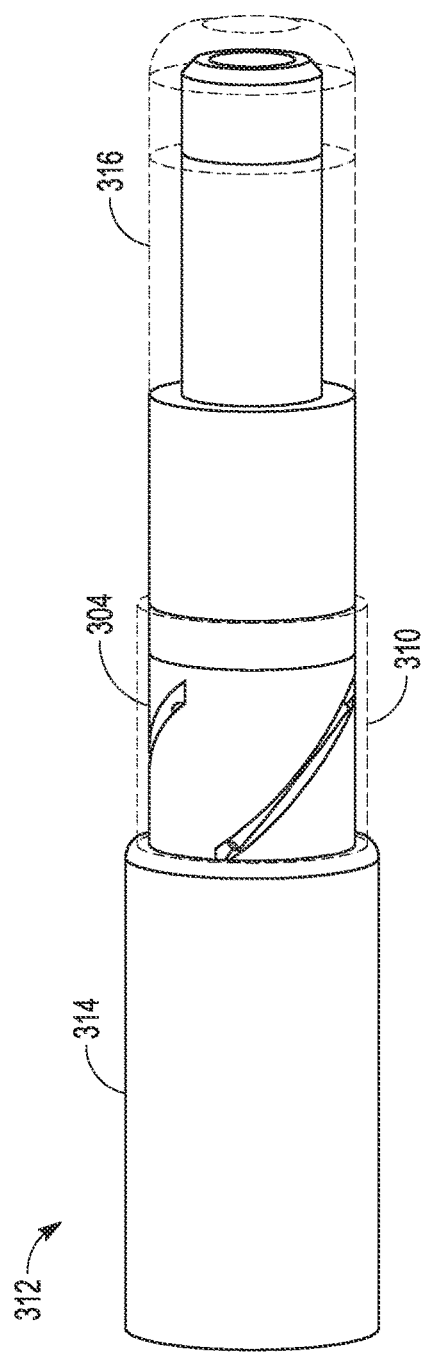
FIG. 3 is an illustration of an example of a connector assembly for a medical device.

FIG. 3 is an illustration of an example of a connector assembly 312 for a medical device. The assembly includes a cylindrical core 304 and a sleeve 310. The sleeve 310 is shown transparent so that the cylindrical core 304 and the slots of the cylindrical core can be seen. A lead is inserted into the insertion end 314 of the assembly and extends to the end cap 316 of the assembly. The insertion end 314 and end cap 316 may be comprised of plastic. The connector assembly 312 may be included in a header block, such as in header connector 155 in FIG. 1. One header block may include multiple connector assemblies.

Figure 4:
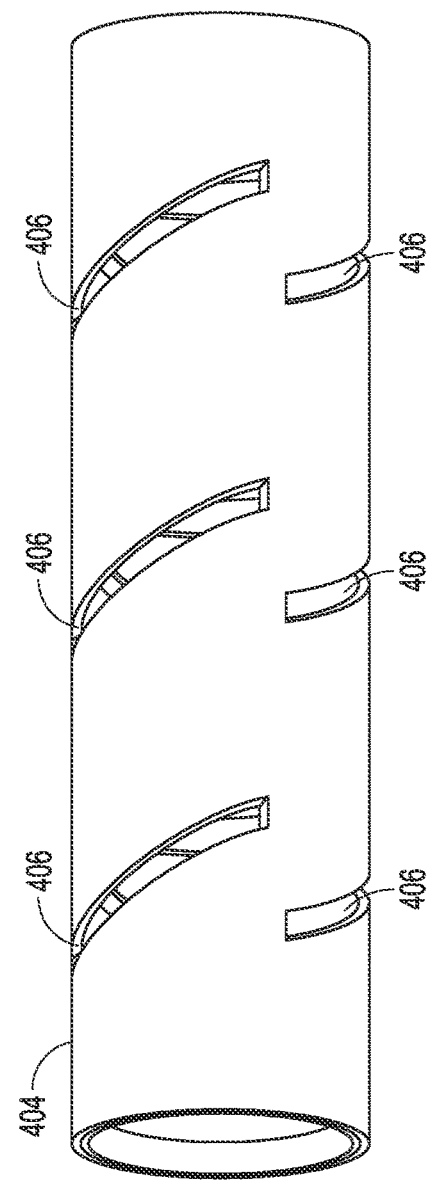
FIG. 4 is an illustration of an example of a cylindrical core for a connector subassembly for a medical device.

FIG. 4 is an illustration of another example of a cylindrical core 404 for a connector subassembly for a medical device. The connector subassembly provides a mechanical connection and electrical contact for a lead with three electrical contacts arranged in series on the lead. The cylindrical core 404 is similar to the example in FIG. 2, but the cylindrical core 404 is longer and includes three sets of slots 406. Each set of slots is positioned along the length of the cylindrical core to coincide with the position of the electrical contacts of the lead. The core can be pre-molded with the slots 406 into which the beams can be pressed.

Figure 5A:
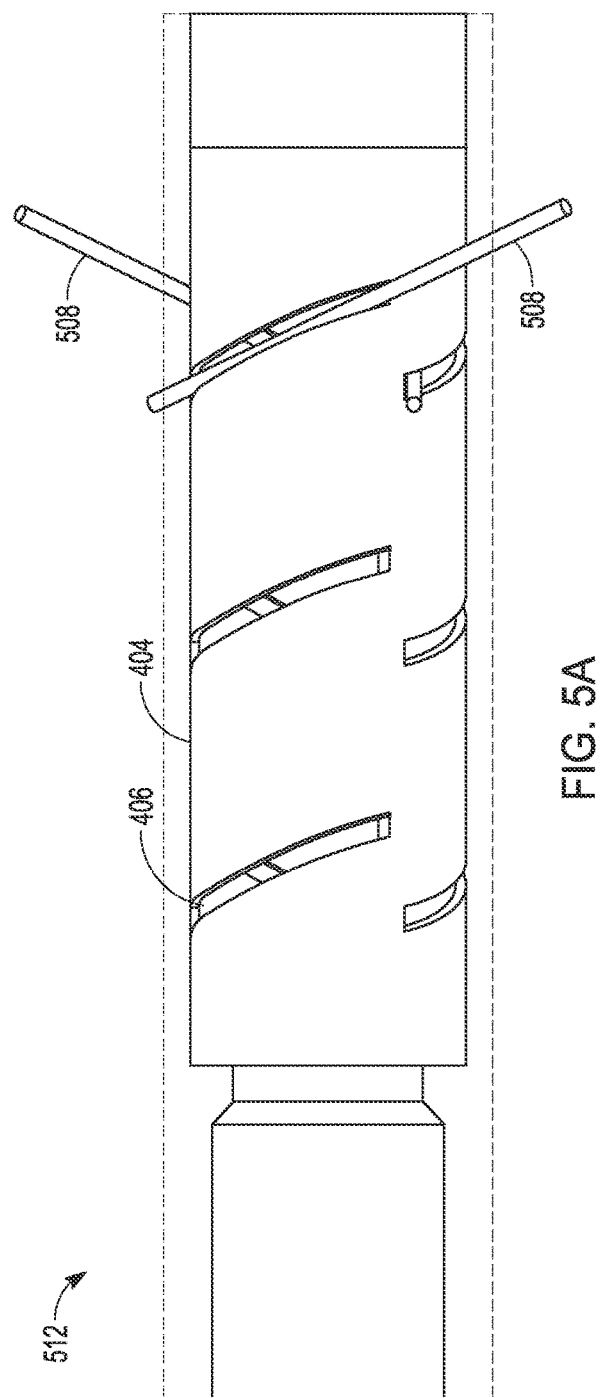
FIGS. 5A-5B are illustrations of portions of another example of a connector assembly for a medical device.
Figure 5B:
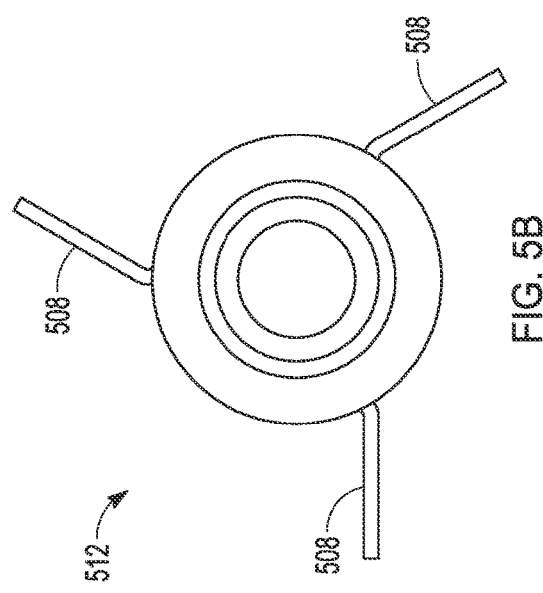

FIG. 5A is an illustration of the cylindrical core 404 of FIG. 4 and portions of a connector assembly 512 that includes the core. Beams 508 are shown placed into the slots 406 of the cylindrical core 404. FIG. 5B shows a side view of the connector assembly 512 of FIG. 5A. Three beam elements are shown extending away from the cylindrical core 404. The three beams 508 provide support for the lead and make electrical contact to an electrical contact of the lead. The beams 508 may be wires that are welded together along with a jumper wire to conduct to a feedthrough of the medical device. In variations, one of the beams 508 may be a wire longer than the other beams or wires to conduct to the feedthrough.

Figure 6C:
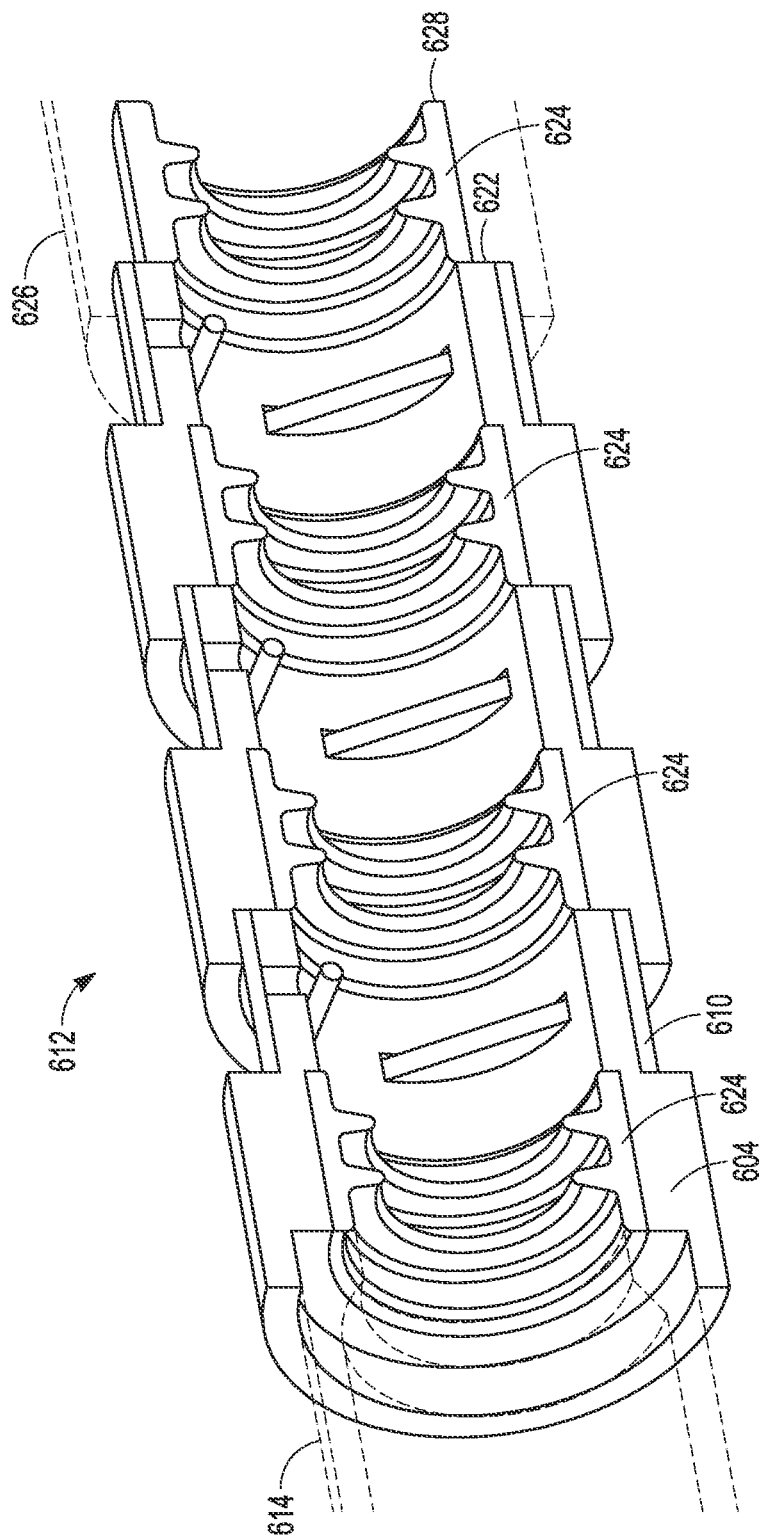

FIGS. 6A-6C are illustrations of another example of a connector assembly 612 for a medical device. The connector assembly 612 includes three modular core connectors 620. The modular core connectors include a cylindrical core 604. Instead of one pre-molded core with three sets of slots for the beam elements, multiple modular core connectors can be built up into the desired number of contacts of the lead that will be inserted into the connector assembly 612.

As in the cylindrical core example 204 of FIG. 2, the cylindrical core 604 of a modular core connector is comprised of nonconductive material. The cylindrical core 604 has a hollow center or bore, and an inside surface and an outside surface. However, the cylindrical core 604 of the modular core connector has two inside diameters and two outside diameters. The inside diameter of a receiving portion of the cylindrical core is slightly greater the outside diameter of a receiving portion of the cylindrical core to allow an insertion end of one module core connector to be inserted into the receiving end of another modular core connector.

The module core connectors 620 can be pressed together (e.g., over core pin tooling) to form the complete bore that receives the lead.

FIG. 6B shows a cutaway view of the example of the connector assembly of FIG. 6A. It can be seen that the insertion end of the modular core connectors 620 includes one or more slots that extend from the outside surface to the inside surface of the insertion portion and beam elements 608 can be placed in the slot openings to contact the lead. A sleeve of conductive material is placed over the outside surface of the insertion end, and a portion of the conductive sleeve 610 of one modular core connector is within the receiving portion of another modular core connector when the module core connectors are connected together.

FIG. 6C is another cutaway view of the example of the connector assembly 612 of FIG. 6A. In the example, the receive portion of a modular core connector includes a first inside diameter and a second inside diameter greater than the first inside diameter to form an interference fit 622 in the receiving portion. The insertion end and the conductive sleeve 610 of one modular core connector is inserted up to the interference fit of the receiving portion of another modular core connector. Each module core connector 620 includes a seal 624 within the receiving portion. The seal 624 may be electrically insulating to provide electrical isolation between modular core connectors 620.

FIG. 6C shows the rightmost modular core connector is inserted into a first cylindrical connector end 626 of the connector assembly. The first cylindrical connector end 626 also includes an interference fit 628 to receive the insertion end of the modular core connector and a seal 624. The connector assembly also includes a second cylindrical connector end 614 that is inserted into the leftmost modular core connector 620.

Returning to FIG. 6B, the first cylindrical connector end 626 is included in an end cap subassembly 616 that includes an end cap 630 and a conductive collar 632. The end cap 630 may be comprised of plastic and the conductive collar 632 may be comprised of metal. The inside diameter of the first cylindrical connector end 626, the conductive collar 632 and end cap 630 are sized to receive an end of a lead. The end of the lead can be conductive, and the conductive collar provides an electrical contact to the lead end. The connector assembly 612 may be included in a header block of a medical device, such as in header connector 155 in FIG. 1. As shown in FIG. 6A, the conductive collar 632 may include an opening to receive a set screw 634 that may help secure the lead in the header connector assembly.

The connector assembly 612 of FIGS. 6A-6C is modular and may be assembled by first attaching the end cap 630 and conductive collar 632, pressing the first cylindrical connector end 626 into the conductive collar 632, pressing the desired number of modular core connectors 620 into the first cylindrical connector end 626 and into each other, and then pressing the second cylindrical connector end 614 into the last modular core connector. If only one modular core connector 620 is used, the connector assembly 612 is similar to the connector assembly 312 of FIG. 3. Multiple connector assemblies may be included in a head connector assembly to receive multiple leads.

Figure 7A:
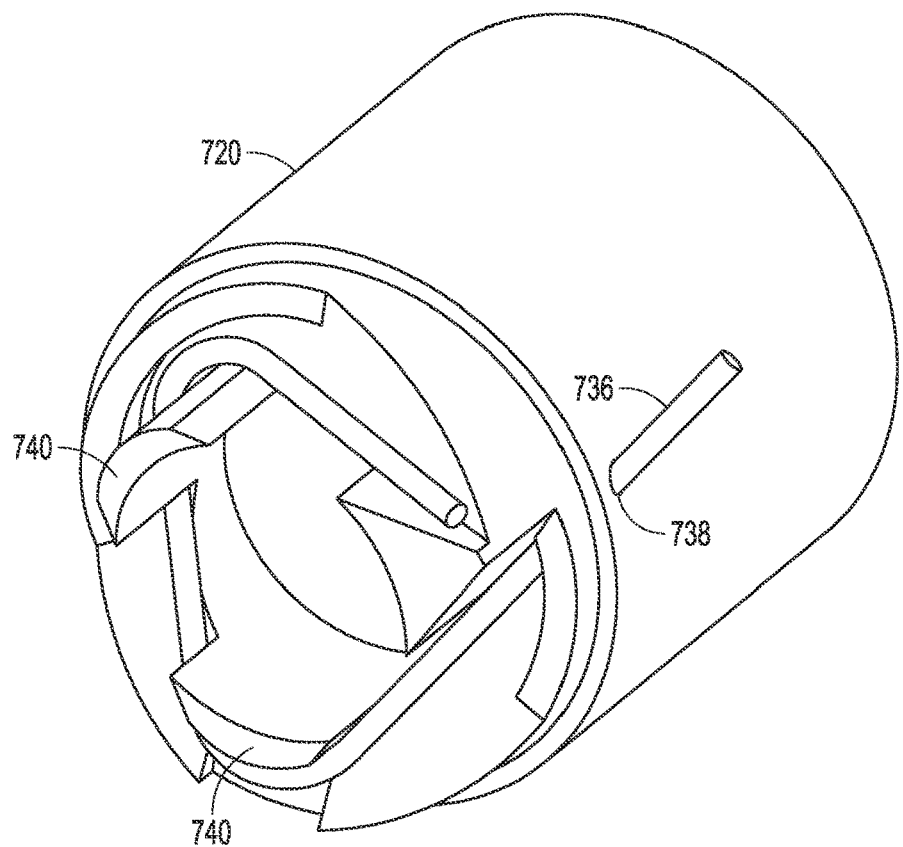
FIGS. 7A-7B are illustrations of an example of a modular core connector for a connector assembly of a medical device.
Figure 7B:
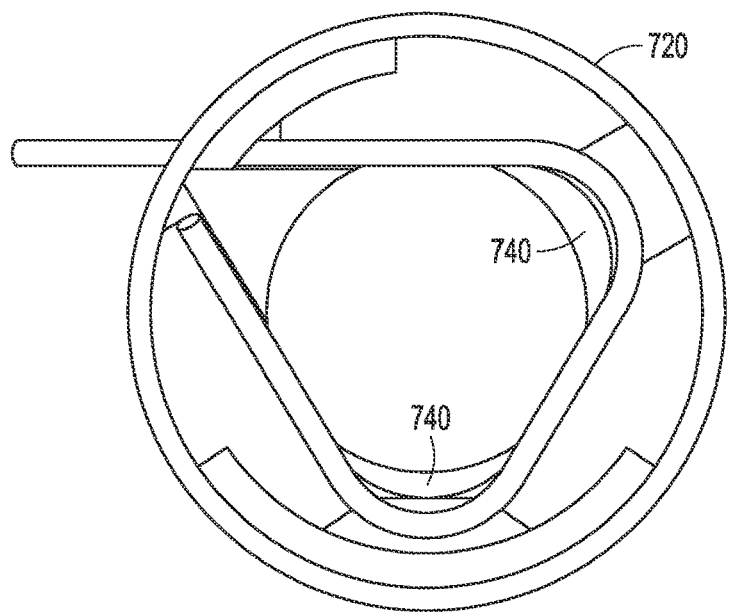

FIGS. 7A-7B are illustrations of another example of a modular core connector 720 for a connector assembly of a medical device. Multiple modular core connectors 720 can be pressed together to form the connector assembly as in the example of FIGS. 6A-6C, but in the modular core connector 720 a continuous wire 736 instead of three beam elements is used to form the electrical contact and support for the inserted lead. Instead of slots, the modular core connector 720 includes tabs 740 and the continuous wire 736 is fed through a small hole 738 and wrapped around the tabs 740 to form bends in the wire which provide electrical contact and support for the inserted lead. In variations, the modular core connector 720 includes slots (e.g., three slots) as in FIG. 2, and the wire is wrapped through the slots. The modular core connector 720 may be pre-molded and one molded segment is combined with wire and an inner seal, and then pressed into an adjacent similar connector to build up the connector assembly.

The devices described herein provide a connector with low insertion force for connecting electrical leads to a medical device. Some examples provide a three-point contact configuration that provides a high contact pressure interface to maintain a robust connection to the leads and still provide a low lead insertion force to ease connector insertion.

ADDITIONAL DESCRIPTION AND EXAMPLES

Example 1 includes subject matter (such as a connector apparatus of a medical device to provide electrical contact to a conductive lead) comprising a cylindrical core including an outside surface, an inside surface, a hollow center having a cross sectional area, and a slot opening in the cylindrical core extending from the outside surface to the inside surface; a beam of conductive material beam placed in the slot opening in the cylindrical core, wherein the beam reduces the cross-sectional area of the hollow center of the cylindrical core; and a sleeve of conductive material placed over the outside surface of the cylindrical core.

In Example 2, the subject matter of Example 1 optionally includes a slot opening in the cylindrical core having a length extending along the cylindrical core in a direction diagonal to a central axis of the cylindrical core.

In Example 3, the subject matter of Example of one or both of Examples 1 and 2 optionally includes a cylindrical core including multiple slot openings that each have a length extending along the cylindrical core in a direction diagonal to a central axis of the cylindrical core, and wherein the apparatus includes multiple beams disposed in the slot openings.

In Example 4, the subject matter of Example of one or both of Examples 1 and 2 optionally includes a cylindrical core including multiple slot openings and the beam of conductive material is a wire with a number of bends, and the wire is arranged in the multiple slot openings.

In Example 5, the subject matter of Example 4 optionally includes a cylindrical core including three slot openings that each have a length extending along the cylindrical core in a direction diagonal to a central axis of the cylindrical core, and the wire includes two bends.

In Example 6, the subject matter of one or any combination of Examples 1-5 optionally includes the beam being flexible.

Example 7 includes subject matter (such as connector assembly for a medical device) or can optionally be included with one or any combination of Examples 1-6 to include such subject matter, comprising a modular core connector having a cylindrical shape and comprised of nonconductive material. The modular core includes an insertion portion having an outside diameter and including an outside surface, an inside surface, a hollow center having a cross sectional area, and a slot opening extending from the outside surface to the inside surface; a receiving portion having an inside diameter and an outside diameter greater than the outside diameter of the insertion portion; a beam of conductive material beam placed in the slot opening of the insertion portion, and at least a portion of the beam is arranged within the cross-sectional area of the hollow center of the insertion portion; and a sleeve of conductive material placed over the outside surface of the insertion portion.

In Example 8, the subject matter of Example 7 optionally includes a conductive sleeve including a slot opening matching the slot opening of the modular core and rotated relative to the slot opening of the insertion portion to fix the beam in place.

In Example 9, the subject matter of one or both of Examples 7 and 8 optionally includes a first cylindrical connector end including a first inside diameter and a second inside diameter greater than the first inside diameter to form an interference fit, wherein the insertion end of the modular core connector is inserted into the first cylindrical connector end; and a second cylindrical connector end inserted into the receiving end of the modular core connector.

In Example 10, the subject matter of one or any combination of Examples 7-9 optionally includes multiple modular core connectors including a first modular core connector and a second modular core connector, wherein the insertion portion of the second modular core connector is inserted into the receiving portion of the first modular core connector.

In Example 11, the subject matter of Example 10 optionally includes an electrically insulating seal disposed within the receiving portion of the first modular core connector and contacting the insertion portion of the second modular core connector.

In Example 12, the subject matter of one or both of Examples 10 and 11 optionally includes a first cylindrical connector end including a first inside diameter and a second inside diameter greater than the first inside diameter to form an interference fit, wherein the insertion portion of a first modular core connector of the multiple modular cores is inserted into the first cylindrical connector end; and a second cylindrical connector end inserted into the receiving portion of another modular core connector of the multiple modular core connectors.

In Example 13, the subject matter of Example 12 optionally includes a first cylindrical connector end including a first inside diameter sized to receive a lead end inserted into the connector assembly and a second inside diameter sized to receive the insertion portion of the first modular core connector, and wherein the first cylindrical connector end is coupled to an electrical contact.

In Example 14, the subject matter of one or any combination of Examples 7-13 optionally includes an insertion portion of the modular core connector including multiple slot openings that each have a length extending along the insertion portion in a direction diagonal to a central axis of the insertion portion, and wherein the apparatus includes multiple flexible beams disposed in the slot openings.

In Example 15, the subject matter of one or any combination of Examples 7-13 optionally includes an insertion portion of the modular core connector including multiple slot openings and the beam of conductive material is a wire with a number of bends, and the wire is arranged in the multiple slot openings.

Example 16 can include subject matter (such as a header connector assembly of a medical device) or can optionally be combined with one or any combination of Examples 1-15 to include such subject matter), comprising multiple modular core connectors and a header block. Each modular core connector having a cylindrical shape and including an insertion portion having an outside diameter and including an outside surface, an inside surface, a hollow center having a cross sectional area, and a slot opening extending from the outside surface to the inside surface; a receiving portion having an inside diameter and an outside diameter greater than the outside diameter of the insertion portion; a beam of conductive material beam placed in the slot opening of the insertion portion, and at least a portion of the beam is arranged within the cross-sectional area of the hollow center of the insertion portion; and a sleeve of conductive material placed over the outside surface of the insertion portion. The multiple modular core connectors are arranged within the header block and the header block includes multiple electrical contacts contacting the sleeve of conductive material of the multiple modular core connectors.

In Example 17, the subject matter of Example 16 optionally includes the multiple modular core connectors that include a first modular core connector and a second modular core connector, wherein the insertion portion of the second modular core connector is inserted into the receiving portion of the first modular core connector.

In Example 18, the subject matter of Example 17 optionally includes an electrically insulating seal disposed within the receiving portion of the first modular core connector and contacting the insertion portion of the second modular core connector.

In Example 19, the subject matter of one or both of Examples 17 and 18 optionally includes a first cylindrical connector end disposed within the header block and including a first inside diameter and a second inside diameter greater than the first inside diameter to form an interference fit, wherein an insertion portion of a first modular core connector of the multiple modular cores is inserted into the first cylindrical connector end; and a second cylindrical connector end disposed within the header block and inserted into a receiving portion of another modular core connector of the multiple modular core connectors.

In Example 20, the subject matter of Example 19 optionally includes a first cylindrical connector end including a first inside diameter sized to receive a conductive lead end inserted into the connector assembly and a second inside diameter sized to receive the insertion end of the first modular core connector, and wherein the first cylindrical connector end includes an electrical contact positioned to contact the conductive lead end.

The non-limiting Examples can be combined in any permutation or combination. The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A connector apparatus of a medical device to provide electrical contact to a conductive lead, the apparatus comprising:
   a cylindrical core including an outside surface, an inside surface, a hollow center having a cross sectional area, and multiple slot openings at evenly spaced locations in the cylindrical core and extending from the outside surface to the inside surface;
   at least one beam of conductive material placed in the multiple slot openings in the cylindrical core, wherein the at least one beam reduces the cross-sectional area of the hollow center of the cylindrical core at the locations of the multiple slot openings; and
   a sleeve of conductive material placed over the outside surface of the cylindrical core, wherein the conductive sleeve includes slot openings matching the slot openings of the cylindrical core and the slot openings of the conductive sleeve are rotated relative to the slot openings of the cylindrical core to fix the at least one beam in place.

2. The apparatus of claim 1, wherein each slot opening of the multiple slot openings in the cylindrical core has a length extending along the cylindrical core in a direction diagonal to a central axis of the cylindrical core.

3. The apparatus of claim 1, wherein the multiple slot openings each have a length extending along the cylindrical core in a direction diagonal to a central axis of the cylindrical core, and wherein the at least one beam includes multiple beams disposed in the slot openings.

4. The apparatus of claim 1, wherein the at least one beam is flexible.

5. The apparatus of claim 1, wherein the at least one beam of conductive material is a wire with a number of bends, and the wire is arranged in the multiple slot openings.

6. The apparatus of claim 5, wherein the cylindrical core includes three slot openings that each have a length extending along the cylindrical core in a direction diagonal to a central axis of the cylindrical core, and the wire includes two bends.

7. A connector assembly for a medical device, the connector assembly comprising:
   a modular core connector having a cylindrical shape and comprised of nonconductive material, the modular core connector including:
      an insertion portion having an outside diameter and including an outside surface, an inside surface, a hollow center having a cross sectional area, and a slot opening extending from the outside surface to the inside surface;
      a receiving portion having an inside diameter and an outside diameter greater than the outside diameter of the insertion portion;
      a beam of conductive material beam placed in the slot opening of the insertion portion, and at least a portion of the beam is arranged within the cross-sectional area of the hollow center of the insertion portion; and
   a sleeve of conductive material placed over the outside surface of the insertion portion, wherein the conductive sleeve includes a slot opening matching the slot opening of the modular core and rotated relative to the slot opening of the insertion portion to fix the beam in place.

8. The connector assembly of claim 7, including:
   a first cylindrical connector end including a first inside diameter and a second inside diameter greater than the first inside diameter to form an interference fit, wherein the insertion end of the modular core connector is inserted into the first cylindrical connector end; and
   a second cylindrical connector end inserted into the receiving end of the modular core connector.

9. The connector assembly of claim 7, wherein the insertion portion of the modular core connector includes multiple slot openings that each have a length extending along the insertion portion in a direction diagonal to a central axis of the insertion portion, and wherein the apparatus includes multiple flexible beams disposed in the slot openings.

10. The connector assembly of claim 7, wherein the insertion portion of the modular core connector includes multiple slot openings and the beam of conductive material is a wire with a number of bends, and the wire is arranged in the multiple slot openings.

11. The connector assembly of claim 7, including multiple modular core connectors including a first modular core connector and a second modular core connector, wherein the insertion portion of the second modular core connector is inserted into the receiving portion of the first modular core connector.

12. The connector assembly of claim 11, including an electrically insulating seal disposed within the receiving portion of the first modular core connector and contacting the insertion portion of the second modular core connector.

13. The connector assembly of claim 11, including:
a first cylindrical connector end including a first inside diameter and a second inside diameter greater than the first inside diameter to form an interference fit, wherein the insertion portion of a first modular core connector of the multiple modular cores is inserted into the first cylindrical connector end; and
a second cylindrical connector end inserted into the receiving portion of another modular core connector of the multiple modular core connectors.

14. The connector assembly of claim 13, wherein the first cylindrical connector end includes a first inside diameter sized to receive a lead end inserted into the connector assembly and a second inside diameter sized to receive the insertion portion of the first modular core connector, and wherein the first cylindrical connector end is coupled to an electrical contact.

15. A header connector assembly of a medical device, the header connector comprising:
multiple modular core connectors, each modular core connector having a cylindrical shape and including:
an insertion portion having an outside diameter and including an outside surface, an inside surface, a hollow center having a cross sectional area, and a slot opening extending from the outside surface to the inside surface;
a receiving portion having an inside diameter and an outside diameter greater than the outside diameter of the insertion portion;
a beam of conductive material beam placed in the slot opening of the insertion portion, and at least a portion of the beam is arranged within the cross-sectional area of the hollow center of the insertion portion; and
a sleeve of conductive material placed over the outside surface of the insertion portion; and
a header block, wherein the multiple modular core connectors are arranged within the header block and the header block includes multiple electrical contacts contacting the sleeve of conductive material of the multiple modular core connectors.

16. The header connector assembly of claim 15, wherein the multiple modular core connectors include a first modular core connector and a second modular core connector, wherein the insertion portion of the second modular core connector is inserted into the receiving portion of the first modular core connector.

17. The header connector assembly of claim 16, including an electrically insulating seal disposed within the receiving portion of the first modular core connector and contacting the insertion portion of the second modular core connector.

18. The header connector assembly of claim 16, including:
a first cylindrical connector end disposed within the header block and including a first inside diameter and a second inside diameter greater than the first inside diameter to form an interference fit, wherein an insertion portion of a first modular core connector of the multiple modular cores is inserted into the first cylindrical connector end; and
a second cylindrical connector end disposed within the header block and inserted into a receiving portion of another modular core connector of the multiple modular core connectors.

19. The header connector assembly of claim 18, wherein the first cylindrical connector end includes a first inside diameter sized to receive a conductive lead end inserted into the connector assembly and a second inside diameter sized to receive the insertion end of the first modular core connector, and wherein the first cylindrical connector end includes an electrical contact positioned to contact the conductive lead end.

* * * * *